United States Patent [19]

Clark et al.

[11] 4,363,913

[45] Dec. 14, 1982

[54] PREPARATION OF 2-AMINOBENZOTHIAZOLES

[75] Inventors: R. Donald Clark; Herman S. Pridgen, both of Kingsport, Tenn.

[73] Assignee: Eastman Kodak Company, Rochester, N.Y.

[21] Appl. No.: 246,496

[22] Filed: Mar. 23, 1981

[51] Int. Cl.³ ............................................ C07D 277/82
[52] U.S. Cl. .................................... 548/164; 548/161
[58] Field of Search ............................. 548/161, 164

[56] References Cited

U.S. PATENT DOCUMENTS 3,981,883 9/1976 Niess ................................. 548/212
4,113,732 9/1978 Opgenorth et al. ............... 548/164

Primary Examiner—David B. Springer
Attorney, Agent, or Firm—Gary C. Bailey; J. Frederick Thomsen; Daniel B. Reece III

[57] ABSTRACT

Disclosed is a process for the preparation of 2-aminobenzothiazoles by the oxidative ring closure of an arylthiourea which comprises contacting the arylthiourea with sulfuric acid and a catalytic amount of a bromine compound.

5 Claims, No Drawings

PREPARATION OF 2-AMINOBENZOTHIAZOLES

This invention relates to the preparation of 2-aminobenzothiazoles by the oxidative ring closure of an arylthiourea.

The preparation of unsubstituted and substituted benzothiazoles by the oxidative ring closure of arylthioureas is well known. See, for example, U.S. Pat. No. 4,113,732 and the prior art discussed therein. In the processes known, chlorine or bromine has been used in equimolar or more than equimolar amounts to oxidatively ring close arylthioureas to obtain 2-aminobenzothiazoles. Those processes are disadvantageous because of the cost of the halogen employed and/or their corrosive properties.

The process of this invention is an improvement in the preparation of 2-aminobenzothiazoles by the oxidative ring closure of an arylthiourea wherein the improvement comprises contacting the arylthiourea with sulfuric acid and a catalytic amount of a bromine compound. The 2-aminobenzothiazole is initially formed as a sulfate salt which can be reacted further to produce other derivatives or converted to the free amine by known means.

The 2-aminobenzothiazoles which can be obtained according to the process of our invention may be unsubstituted or substituted with one or more substituents selected from alkyl, alkoxy, alkylthio, halogen, alkylsulfonyl, arylsulfonyl, nitro, cyano, alkanoylamino, aroylamino, aryl, aralkyl, alkoxycarbonyl, groups having the formula $-CONR^1R^2$ and $-SO_2NR^1R^2$ wherein $R^1$ is hydrogen or alkyl, $R^2$ is $R^1$ or aryl or $R^1$ and $R^2$ collectively can be pentamethylene or 3-oxapentamethylene, etc. The alkyl moieties of these groups generally will be lower alkyl, i.e. containing up to about 4 carbon atoms. The aryl moieties of the above arylsulfonyl, aroylamino and aryl groups will most commonly be phenyl and phenyl substituted with lower alkyl, lower alkoxy or halogen.

Examples of the substituents which can be present on the 2-aminobenzothiazoles obtainable according to the present invention include methyl, ethyl, propyl, isobutyl, methoxy, ethoxy, propoxy, ethylthio, butylthio, acetamido (acetylamino), propionamido, benzamido, methylsulfonyl, butylsulfonyl, benzenesulfonyl, p-tolylsulfonyl, phenyl, p-chlorophenyl, benzyl, phenethyl, p-butoxyphenyl, ethoxycarbonyl, carbamoyl, N-butylcarbamoyl, N,N-diethylcarbamoyl, morpholinocarbonyl, N-phenylsulfamoyl, peperidinosulfamoyl and the like. Ususally the substituted 2-aminobenzothiazoles will contain not more than 2 substituents. The substituted aryl group of the arylthioureas from which the substituted 2-aminobenzothiazoles are derived must, as will be apparent to one skilled in the art, contain at least one unsubstituted ring carbon atom ortho to the point of attachment to the thiourea nitrogen atom. Thus, the arylthioureas employed in and the 2-aminobenzothiazoles obtained from our novel process can be represented by the formulas

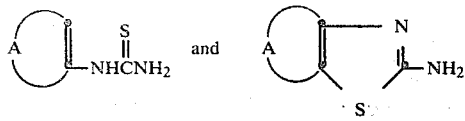

respectively, wherein A represents the atoms necessary to complete a benzene ring, i.e. and usubstituted or substituted butadienyl group

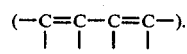

A preferred embodiment of the present invention comprises the oxidative ring closure of an arylthiourea having the formula

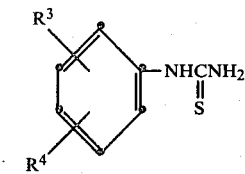

to obtain a 2-aminobenzothiazole (as its sulfate salt) having the formula

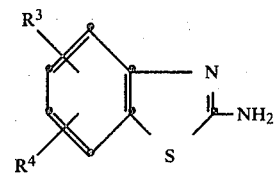

wherein $R^3$ represents hydrogen, lower alkyl, lower alkoxy, chlorine, lower alkylsulfonyl or nitro and $R^4$ represents hydrogen, lower alkyl, lower alkoxy or chlorine. The process of this invention is especially useful for converting phenylthiourea to the sulfate salt of a 2-aminobenzothiazole which then may be converted, without isolation, to the 6-nitrobenzothiazole by the addition of nitric acid to the reaction mixture.

The concentration of the sulfuric acid employed in the process of the invention normally should be at least about 85 percent and preferably is in the range of about 95 to 100 percent. The amount of sulfuric acid used should be at least 3.5 times the weight of the arylthiourea. Although there is no reason why very large amounts of acid could not be used, as a practical matter the sulfuric acid:thiourea weight ratio usually will not exceed about 5.

The particular temperature that gives best results will vary depending on such things as the concentration of the sulfuric acid, the particular arylthiourea employed and the amount of bromine compound used. For example, arylthioureas having electron withdrawing groups such as alkylsulfonyl or nitro will require the use of higher temperatures, e.g. 70°–100° C. whereas other arylthioureas can be converted to the corresponding benzothiazoles using temperatures of about 30° to 60° C. In general, the process can be carried out at about 20° to 120° C. with 30°–100° C. being the preferred range. The use of low reaction rates will result in unacceptably low reaction rates whereas the use of high temperatures causes sulfonation of the benzene ring of the 2-aminobenzothiazole reactant.

The bromine compounds useful in our novel process can be elemental bromine, hydrogen bromide or a bromide salt such as sodium bromine, potassium bromide, ammonium bromide, etc. The amount of bromine catalyst used should be at least 0.01 mole percent based on the moles of arylthiourea used. While amounts as large as 50 mole percent can be used, such large amounts produce no beneficial results and in effect, nullifies athe primary advantage offered by the invention, i.e. the use of a catalytic amount of a bromine compound. Preferably, the bromine compound is elemental bromine and the amount of bromine compound used is about 0.1 to 5.0, especially about 0.1 to 1.0, mole percent based on the moles of arylthiourea used. The process of this invention is further illustrated by the following examples.

EXAMPLE 1

To a solution of p-tolylthiourea (116 g., 1.0 mol) in 300 ml. og 98% sulfuric acid at 5°–10° C. is added bromine (8 g.) over a period of 30 minutes . During the bromine addition the temperature is allowed to rise to 12° C. and the evolution of gas begins. The temperature is allowed to gradually rise at such a rate that gas evolution does not become too vigorous with most of the gas evolution having been completed when the temperature reaches 25° C. The reaction mixture then is warmed to 35° C. and held at that temperature for 2 hours. When the reaction was complete (as determined by thin layer chromatography) nitrogen is passed through the reaction mixture with vigorous stirring for 2 hours. The light yellow solution is cooled to 15° C., poured onto 500 g. ice, stirred well and the solid is filtered off. The solid is reslurried in 800 ml. water and the mixture is made basic with 28% aqueous ammonia. The solid is filtered off, washed with water and dried. The yield of 2-amino-6-mehtyl- benzothiazole (m.p. 182–184° C.) is 95%. The use of sodium bromide in the above procedure gives similar results although the reaction rate is slower.

EXAMPLE 2

A solution of phenylthiourea (152 g., 1.0 mol) in 300 ml. of 98% sulfuric acid is treated with bromine (8 g.) according to the procedure described in Example 1 to obtain a reaction mixture of the sulfate salt of 2-aminobenzothiazothiazole. The solution is cooled to 10° C. and stirred . 70 G. (1.1 mole) of 98% nitric acid is added over a 45 minute period. Nitrogen is bubbled through the solution prior to and during the nitric acid addition. The solution is allowed to warm to 15° C. and then is poured over 500 g ice. The product is recovered as in Example 1 to give 185 g. (95%) of 2-amino-6-nitrobenzothiazole (m.p. 240°–243° C.).

EXAMPLE 3

To a solution of p-nitrophenylthiourea (19.7 g., 0.1 mol) in 40 ml. of 98% sulfric acid is added 1.0 g. of 48% aqueous HBr. The temperature rises about 10° C. with the evolution of gas. The temperature is controlled at 45°–50° C. for 1½ hours, then raised to 90° C. and maintained at that temperature for 5 hours. The mixture then is sparged with nitrogen for 30 minutes and cooled to 20° C. Water (80 ml.) is added with rapid stirring and the product which precipitates is filtered off, washed with acetone and dried. The yield of 2-amino-6-nitrobenzothiazole, sultate salt is 25.0 g. (86%).

EXAMPLE 4

To a solution of p-tolylthiourea 83.0 g. (0.5 mol) in 150 ml. of 98% sulfuric acid is added, in 1.0 g. increments every 30 minutes, 6.0 g. of 48% aqueous HBr while controlling the temperature at 45°–50° C. The mixture is stirred at 45°–55° C. for 4 hours and nitrogen is blown through it for 1 hour. After cooling the mixture to room temperature, 150 ml. methanol is added. Atter cooling further to 10° C. the resulting precipitate is filtered off, washed with three 100 ml. portions of acetone and dried to yield 123 g. (94%) of the sulfate salt of 2-amino-6-mehtylbenzothiazole assaying 99.4%.

EXAMPLE 5

To a solution heated to 60° C., of p-mehtylsulfonylphenylthiourea 15.0 g. (0.06 mol) in 30.0 ml. of 98% sulfuric acid is added 1.4 g. of 48% aqueous HBr in three 0.3 g. portions followed by a final 0.5 g. portion. Upon addition of the first portion the reaction mixture rised to about 75° C. After allowing the mixture to cool to 500° C. and maintaining it at that temperature for 30 minutes, a second 3.0 g. portion of the aqueous HBr is added and the temperature is controlled at 50° C. for 30 minutes. A third 0.3 g. portion is added and the temperature is maintained at 50° C. for 30 minutes and then at 65° C. for 1½ hours. The final portion of aqueous HBr is added and the mixture is heated with stirring first at 65°C. for 2 hours and then at 90° C. for 1½ hours. After sparging the mixture with nitrogen for 30 minutes, the mixture is cooled and poured into 100 ml. of water. After cooling the resulting mixture, the precipitate is filtered off, washed with acetone and dried. The yield of 2-amino-6-methylsulfonylbenzothiazole, sulfate salt is 79.9%.

EXAMPLE 6

To a solution of p-chlorophenylthiourea (93.3 g., 0.5 mol) in 150 ml. of 98% sulfuric acid is added 6.0 g. of 48% aqueous HBr in 1.0 g. portions every 30 minutes while the temperature is controlled at 45°–50° C. The mixture is maintained at 45°–50°C. for 1½ hours then at 65°–70° C. for 6 hours. The mixture is cooled and 250 ml. of methanol is added with rapid stirring causing the temperature to rise to about 70° C. The mixture then is cooled and the precipitated product is filtered off, washed with three 150 ml. portions of acetone and dried. The yield of 2-amino-6-chlorobenzothiazole is 128.4 g. (92%).

Although the invention has been described in considerable detail with particular reference to certain preferred embodiments thereof, variations and modifications can be effected within the spirit and scope of the invention.

We claim:

1. In a process for the preparation of 2-aminobenzothiazoles by the oxidative ring closure of an arylthiourea, the improvement comprising the step of contacting the arylthiourea dissolved in sulfuric acid with a catalytic amount of bromine, hydrogen bromide, sodium bromide, potassium bromide or ammounium bromide.

2. Process of claim 1 wherein the concentration of the sulfuric acid is at least about 85 percent, the amount of sulfuric acid used is at least 3.5 times the weight of the arylthiourea, the contacting is carried out at a temperature of about 20° to 120° C. and the amount of bromine compound is about 0.1 to 5.0 mole percent based on the arylthiourea.

3. In a process for the preparation of 2-aminobenzothiazole having the formula

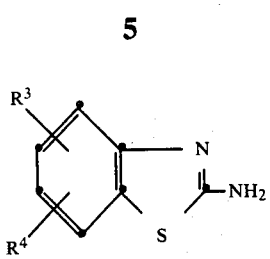

by the oxidative ring closure of an arylthiourea having the formula

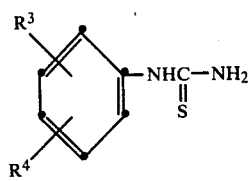

the improvement comprising the step of contacting the aryl thiourea dissolved in sulfuric acid having a concentration of at least about 85% with a catalytic amount of bromine of hydrogen bromide at a temperature of about 20° to 120° C., wherein $R^3$ represents hydrogen, lower alkyl, lower alkoxy, chlorine, lower alkylsulfonyl or nitro and $R^4$ represents hydrogen, lower alkyl, lower alkoxy or chlorine.

4. Process according to claim 3 wherein the concentration of the sulfuric acid is about 95 to 100%, the amount of sulfuric acid is at least about 3.5 times the weight of the arylthiourea, the temperature is about 30°-100° C. and the amount of bromine or hydrogen bromide is about 0.1 to 1.0 mole percent based on the moles of arylthiourea used.

5. In a process for the preparation of 2-aminobenzothiazole, 2-amino-6-methylbenzothiazole, 2-amino-6-nitrobenzothiazole, 2-amino-6-methylsulfonylbenzothiazole or 2-amino-6-chlorobenzothiazole by the oxidative ring closure of phenylthiourea, p-tolythiourea, p-nitrophenylthiourea, p-methylsulfonylphenylthiourea or p-chlorophenylthiourea, the improvement comprising the step of contacting the arylthiourea dissolved in sulfuric acid with a catalytic amount of bromine, hydrogen bromide, sodium bromide, potassium bromide or ammonium bromide.

* * * * *